(12) United States Patent
Koudelka et al.

(10) Patent No.: US 8,306,760 B1
(45) Date of Patent: Nov. 6, 2012

(54) DEFECT DETECTION ON OPTICAL FIBER SPECIMEN USING 3D SURFACE DATA

(75) Inventors: Peter D. Koudelka, St. Paul, MN (US); Eric K. Lindmark, Shoreview, MN (US); Alan J. Blair, St. Paul, MN (US)

(73) Assignee: Promet International, Inc., Shoreview, MN (US)

( * ) Notice: Subject to any disclaimer, the term of this patent is extended or adjusted under 35 U.S.C. 154(b) by 467 days.

(21) Appl. No.: 12/488,993

(22) Filed: Jun. 22, 2009

Related U.S. Application Data

(60) Provisional application No. 61/074,443, filed on Jun. 20, 2008.

(51) Int. Cl.
*G01B 5/28* (2006.01)
*G06K 9/00* (2006.01)
(52) U.S. Cl. .......................... 702/35; 382/108
(58) Field of Classification Search ............ 702/35–36, 702/40, 66–67, 69–73, 81, 84, 127, 182–183, 702/185, 189; 382/108, 141, 145–146, 149, 382/152, 154; 356/73.1, 237.1, 450, 477, 356/485, 489, 511, 600–601, 625–640
See application file for complete search history.

(56) References Cited

U.S. PATENT DOCUMENTS 7,312,859 B2 12/2007 Koudelka et al.
2008/0074676 A1 3/2008 Koudelka et al.

OTHER PUBLICATIONS

Yin et al., Vision-Based Automatic Endface Inspection of Single-Fibre Optical Connectors, 2005, Meas. Sci. Technol. 16, pp. 966-976.*

* cited by examiner

*Primary Examiner* — Toan M Le
(74) *Attorney, Agent, or Firm* — Leanne Taveggia Farrell; Westman, Champlin & Kelly, P.A.

(57) ABSTRACT

A computing system includes an interferometer and a processor. The interferometer is configured to generate at least two phase shifted images of an optical fiber specimen. The processor is configured to acquire the at least two phase shifted images from the interferometer, generate a first intermediate data set based on the at least two acquired phase shifted images and perform two-dimensional defect detection on the first intermediate data set.

20 Claims, 9 Drawing Sheets

DEFECT DETECTION ON OPTICAL FIBER SPECIMEN USING 3D SURFACE DATA

The present application is based on and claims the benefit of U.S. provisional patent application Ser. No. 61/074,443, filed Jun. 20, 2008, the content of which is hereby incorporated by reference in its entirety.

BACKGROUND

A fiber optic connector requires a high-quality, optical-grade endface surface to maximize coupling efficiency and ensure proper operation of the fiber. Generally, a fiber endface has a desirable geometry or topography, such as a desirable radius of curvature, apex offset, fiber height and angle. The fiber endface also has an acceptable surface quality. Examples of surface defects include scratches, digs and other contaminants. A desirable surface geometry and acceptable surface quality can be achieved through an optical polishing process and tested using two different instruments or two separate processes within a single instrument.

The surface quality of the fiber can be measured using an optical microscope to magnify any scratches, digs, or small irregularities that might be present on the fiber surface. The microscope can be either visual or it can utilize an area array detector (e.g. camera) to generate a digital image. If the microscope is visual, then an operator makes a subjective surface quality judgment by considering the approximate size and shape of the scratches present within a predefined area of the fiber endface. If an area array detector is used, two-dimensional image processing algorithms can extract defects.

The geometry of a fiber endface can be measured with an interferometric device which uses various optical interference techniques to generate a three-dimensional map of the fiber endface. Interferometers effectively generate images of a surface being tested. However, these images are superimposed with optical fringe patterns that obscure large areas of the sample and cannot, therefore, be used to visually search for defects. Therefore, it can be necessary to use a separate optical instrument or separate process in an imaging system to complete the microscope inspection portion of the test and identify small defects.

SUMMARY

A computing system for detecting defects on an optical fiber specimen endface includes an interferometer and a processor. The interferometer is configured to generate at least two phase shifted images of an optical fiber specimen. The processor is configured to acquire the at least two phase shifted images from the interferometer, generate a first intermediate data set based on the at least two acquired phase shifted images and perform two-dimensional defect detection on the first intermediate data set.

The computing system can also generate phase data and phase modulation data based on the at least two acquired phased shifted images. Based on the phase data and the phase modulation data, a second intermediate data set can be generated. Two-dimensional defect detection can also be performed on the second intermediate data set.

DETAILED DESCRIPTION

Embodiments, described in detail below, include the use of 3D surface and phase modulation information, collected as part of the interferometric measurement process for gathering topography data, to detect defects and/or evaluate the surface quality of the surface being tested. This can augment or completely eliminate the need to perform a second, dedicated defect detection or surface quality inspection step using a microscope or other imaging device.

Embodiments allow all types of interferometers, including Mireau interferometer microscope objectives, to perform effective defect analysis using a data set from the 3D interferometric surface scan and fast 2D array image processing techniques. The need to perform a separate visual inspection test is eliminated.

Figure 1:
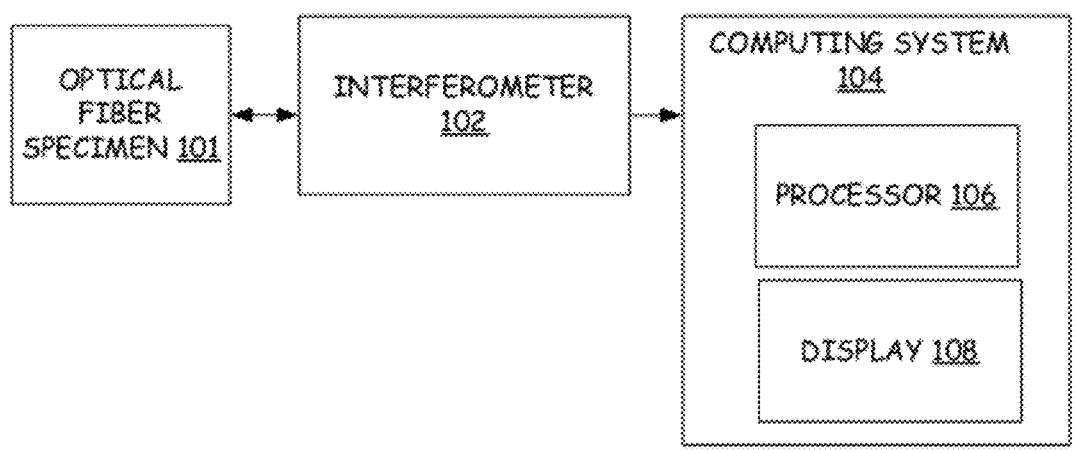
FIG. 1 illustrates a computing system for executing embodiments of the disclosure.

As illustrated in FIG. 1, an interferometer 102 for testing a surface of an optical fiber specimen or sample 101 can be accomplished in suitable computing system environments. For example, interferometer 102 can be coupled to a computing system 104 having a processor 106 and display 108. Examples of well known computing systems, that are suitable for use with testing optical fiber specimens include, but are not limited to, personal computers, server computers, handheld or laptop devices, multiprocessor systems, microprocessor-based systems, set top boxes, programmable consumer electronics, network PCs, minicomputers, mainframe computers, distributed computing environments that include any of the above systems or devices, and the like.

Embodiments of defect detection on optical specimens are described below in the general context of computer-executable instructions, such as program modules, being executed by processor 106 in one or more of the devices listed above and being stored on a computer-readable media such as a disc drive or solid state memory, for example. Generally, program modules include routines, programs, objects, components, data structures, etc. that perform particular duties or implement particular abstract data types. Some embodiments are designed to be practiced in distributed computing environments where tasks are performed by remote processing devices that are linked through a communications network. In a distributed computing environment, program modules are located in both local and remote computer storage media (or computer-readable media) including memory storage devices.

The three-dimensional map of an optical ferrule endface produced by an interferometer is a large data set requiring complex three-dimensional processing algorithms to extract information. By utilizing the processing required to produce the three-dimensional map, the data can be converted to two dimensional data and processed for defects using conventional 2D image processing algorithms.

Utilizing the 3D surface data sets has several important advantages over simply using a visual 2D image to locate defects in the 3D structure of the sample being tested. In one instance, searching for small localized defects in 3D space on a nominally curved surface is computationally very intensive and requires significant amounts of time and hardware resources. This is not desirable for most production testing applications. The 3D surface data sets that will be described below have been converted to 2D numerical arrays (see blocks 206 and 210 of FIG. 2) that can be used with existing image processing techniques (see block 214 of FIG. 2), or other standard image processing techniques to quickly and easily locate pixel locations that correspond to defects on the sample being tested. Image processing techniques in this instance would be used to identify small non-geometric groups of adjacent pixels that deviate in intensity (or other property, like color) values from the average of intensity values of other pixels in the image. "Blob" analysis is one example method for defining these groups of pixels. However, other methods are possible. The results of these processed 2D numerical arrays can be summed together (see block 216 of FIG. 2) to effectively identify different types of defects (see block 218 of FIG. 2). For example, results include the number, size, shape, contrast, location and type of defect found in each data set. By comparing the results from different methods, results can be cross-references and more information can be obtained about specific defects and/or eliminate "false" defects. As described above, the overall sensitivity and accuracy of the process is improved.

Using the 3D surface data to detect defects also yields a higher theoretical resolution than would be possible with a typical visual microscope. The lateral resolution of a typical interferometer is determined by the theoretical maximum optical resolution (diffraction limit) of a specific optical system being used to image the fringe pattern on the area detector. For testing of ferrule end-face geometry, this lateral resolution is typically around 1 micron/pixel. However, the resolution in the vertical direction (z-direction) of the 3D surface data is usually much higher. Depending on the quality of the interferometry technique being used, the typical resolution in the vertical plane is about 1-10 nm. This means that the processed 3D surface data has a theoretical resolution in the vertical plane (z-direction) that is 100 to 1,000 times higher than the maximum theoretical resolution in the horizontal plane (xy plane).

Figure 3:
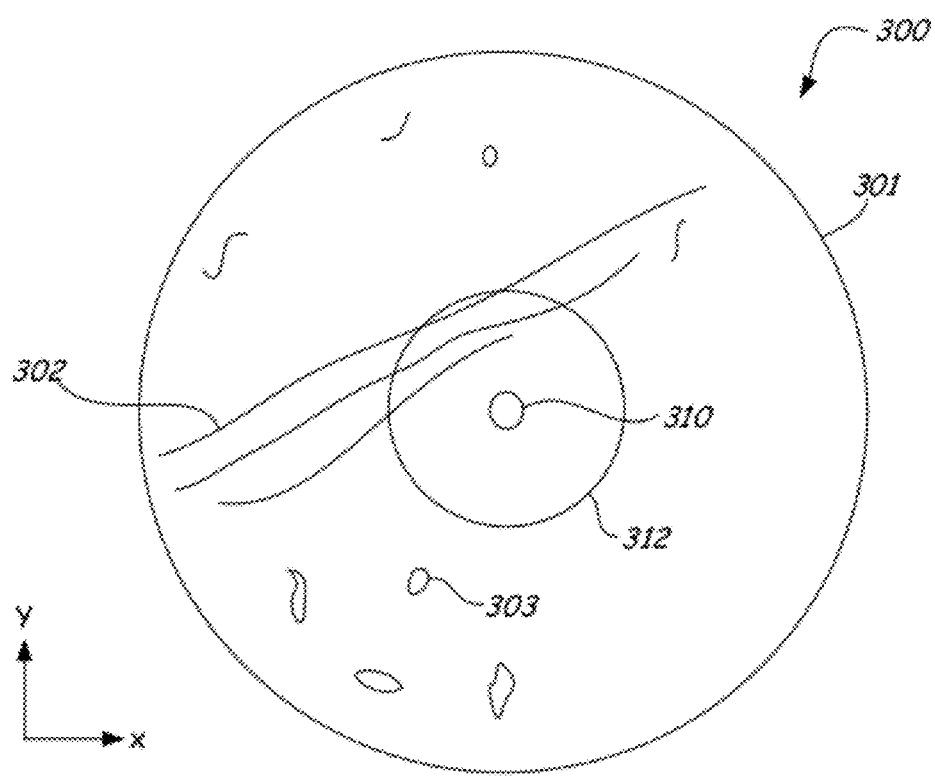
FIG. 3 is a plan view of the endface of an optical fiber specimen.
Figure 4:
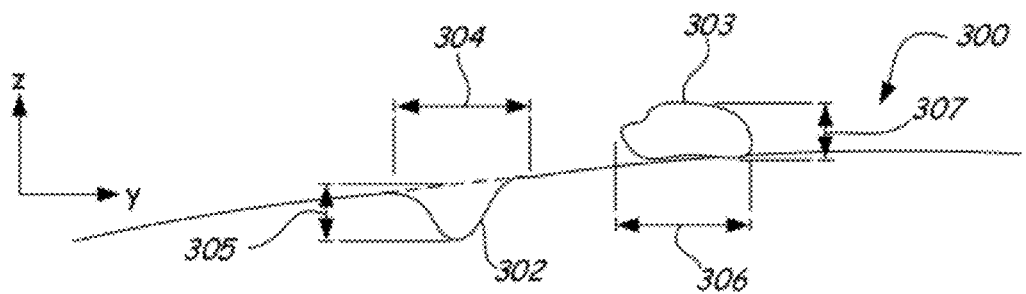
FIG. 4 is a section view of defects that might be found on the optical fiber specimen illustrated in FIG. 3.

FIG. 3 is a plan view of an endface 300 of an optical connector ferrule or other type of optical fiber specimen 301. Optical connector ferrule 301 includes a core 310 and cladding 312. FIG. 4 is a section view of typical defects that might be found on the endface 300 of the optical fiber specimen 301. Endface 300 includes defects. Most surface defects have both a lateral and a vertical component in their structure and can be classified into two categories: surface defects such as scratches or pits 302 and foreign debris or particles 303 on the endface 300. A scratch or a pit will have a lateral component 304 and negative vertical component 305 (FIG. 4). A particle will have a lateral component 306 and a positive vertical component 307 (FIG. 4). Visual defect detection methods rely only on the lateral structure of the defect in the xy plane (as illustrated in FIG. 4) and disregard the vertical structure in the z-direction (as illustrated in FIG. 4). A 3D surface method of defect detection uses the lateral 304, 306 and the vertical 305, 307 components of the defect structure to detect the presence of a surface defect in a specific location. Since the vertical (z-direction) resolution present in the phase data is higher, the sensitivity of defect detection is greatly improved.

Figure 2:
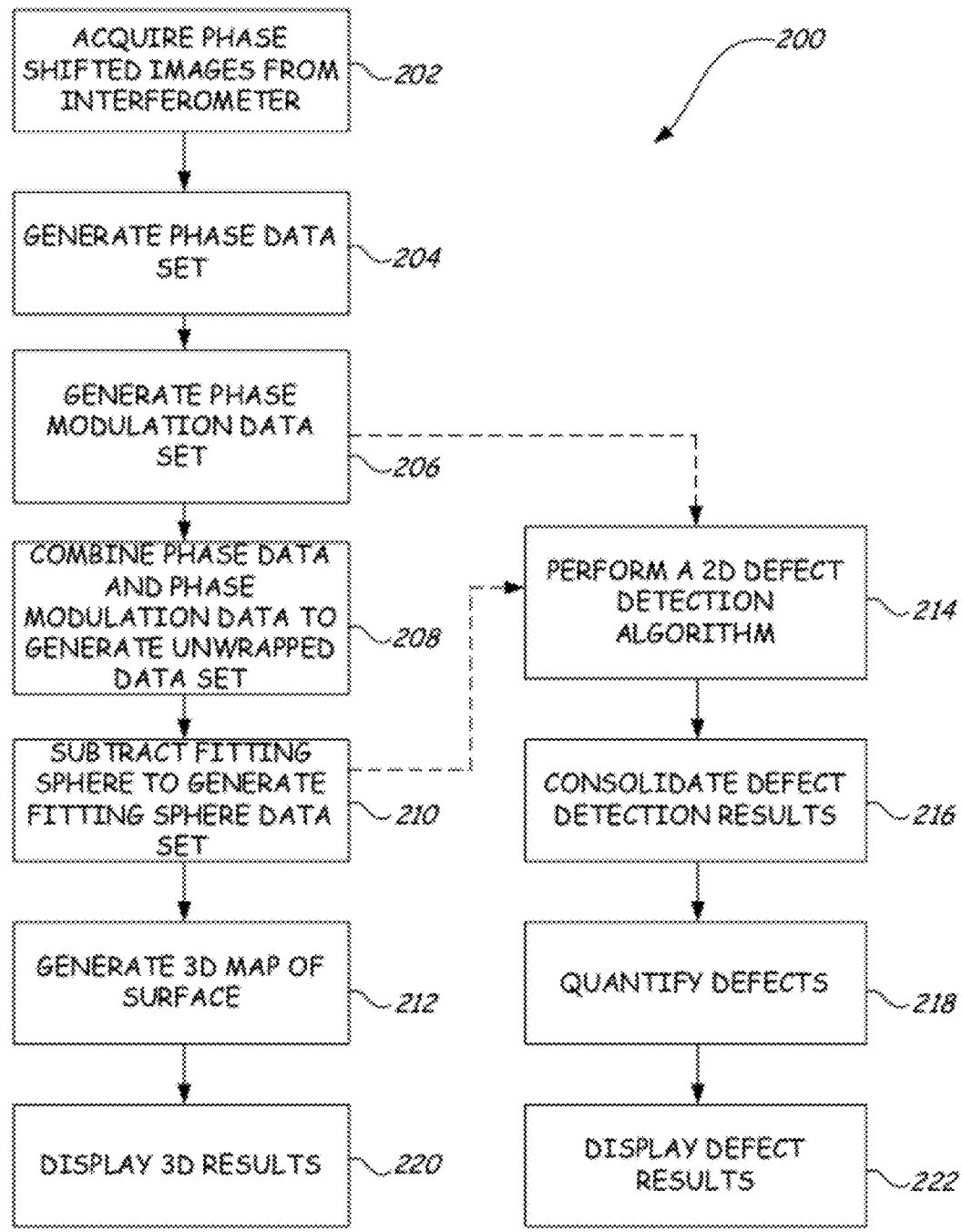
FIG. 2 is a flow chart illustrating a method of detecting defects on an endface of an optical fiber specimen.

FIG. 2 is a flow chart 200 illustrating a method of detecting defects on an endface of a ferrule using intermediate data sets generated during the processing of interference fringe images to generate a 3D map of the surface and measure the shape of the endface. The left side of the flow chart 200 illustrates the generation of a 3D map from a series of images containing interferometric data. The right side of the flow chart 200 illustrates the use of information determined in the process of measuring the shape of the endface that can be used for a 2D numerical array defect detection analysis. In particular, the 3D surface and the phase modulation information obtained with any phase-shifting interferometric instrument can be used to detect defects on the endface.

Figure 5:
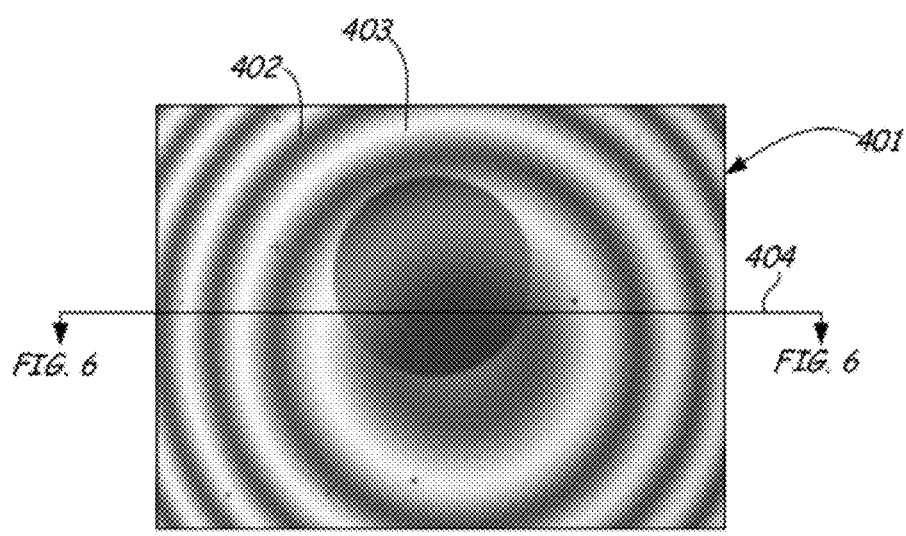
FIG. 5 is an example interferometric fringe image.
Figure 6:
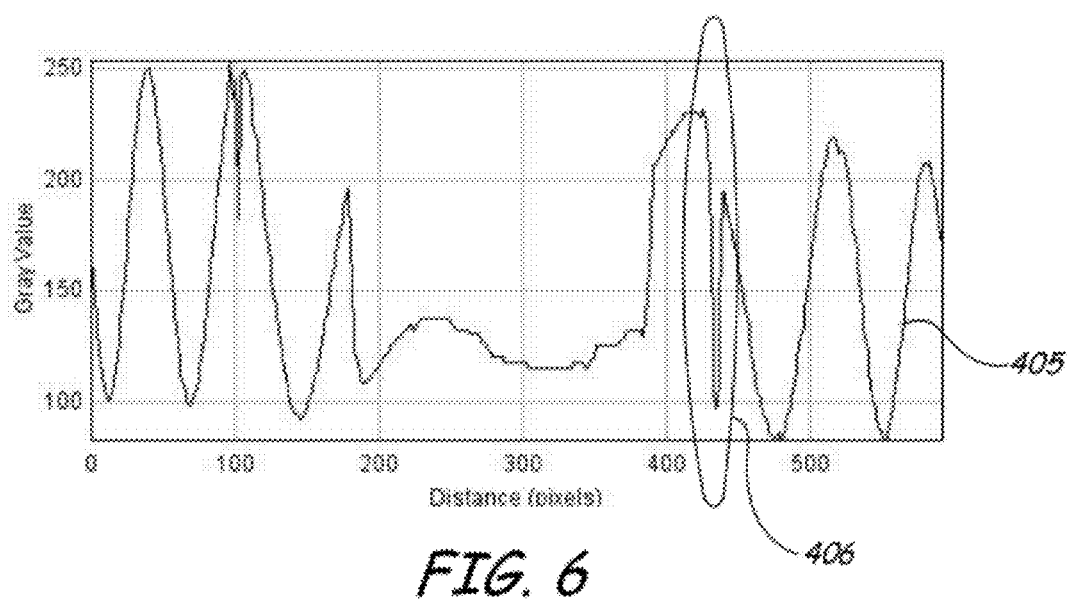
FIG. 6 is a graphical representation of intensity values of select pixels on the fringe image illustrated in FIG. 5.

At block 202, phase shifted images or image frames are acquired from an interferometer. FIG. 5 illustrates an example interferometric fringe image 401 showing how most of the sample being imaged is obscured by the dark rings of the fringe pattern. The interferometer will generate at least two interference images similar to image 401, with a predefined phase shift between each frame. The interference image for radius polished fiber optic connectors appear as a series of light 403 and dark 402 rings corresponding to the height topography of the sample being measured. FIG. 6 illustrates a graphical representation of intensity values for select pixels located along line 404 in FIG. 5. Basically, data across line 404 in the FIG. 5 image is converted into a two-dimensional array of intensity values where each pixel in the image 401 of FIG. 5 corresponds exactly to a location on the sample and a value 405 in the numerical array. Location 406 represents a defect. The 2D arrays for select pixels are used for the data processing required to obtain the 3D map of the sample being tested.

With reference back to FIG. 2, although different types of algorithms can be employed in calculating a 3D map, at least the following steps can be included: generation of phase data as illustrated in block 204, generation of a phase modulation data as illustrated in block 206, combining phase data and phase modulation data to form unwrapped phase data as illustrated in block 208, subtracting sphere fitting information to generate fitting sphere dataset as illustrated in block 210 and the generation of the final 3D map of the surface illustrated in block 212.

Figure 13:
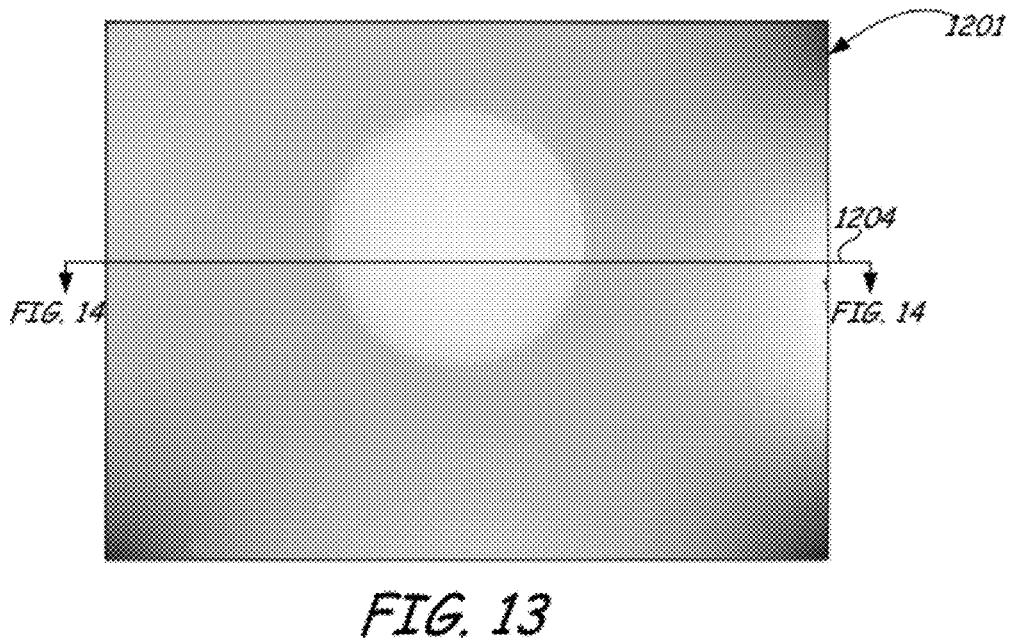
FIG. 13 illustrates an example image of a subtracted and fitted phase plot representing subtracted and fitted phase data.
Figure 14:
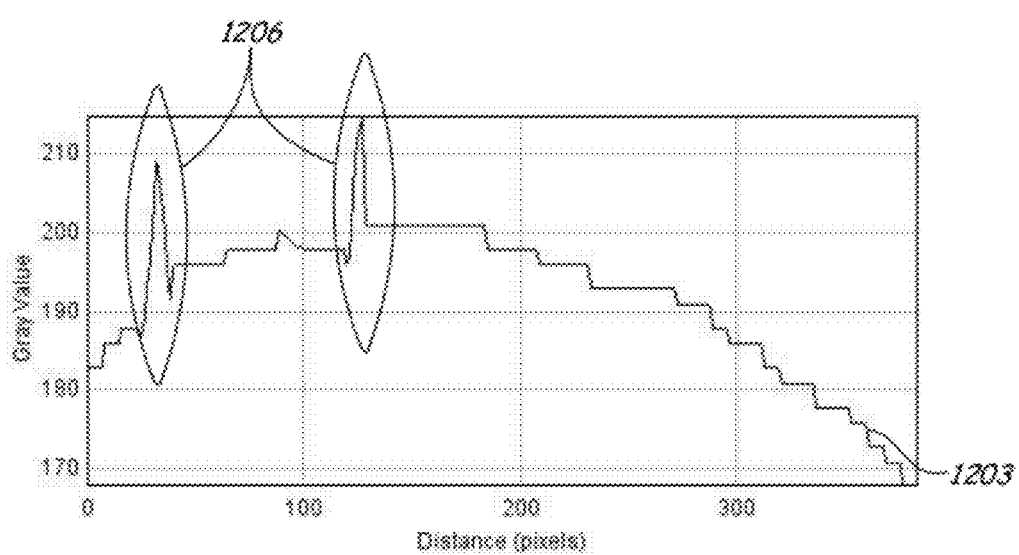
FIG. 14 is a graphical representation of intensity values of select pixels of the subtracted and fitted phase plot on the representative subtracted and fitted phase plot illustrated in FIG. 13.

The data sets generated in blocks 204 through 210 are called intermediate data sets. Intermediate data sets are typically not displayed and only exist as temporary data sets within the computation process. The data sets are 2D numerical arrays that are the same size as the number of pixels present in the original phase shift images acquired from the interferometer. Each one of these 2D numerical arrays can be graphically displayed as a grey-scale image where the intensity value of each pixel in the image corresponds to the value of the corresponding cell of the 2D numerical array. For example light pixels represent high values or high signals and dark pixels represent low values or low signals. Graphical representations of these 2D numerical arrays are displayed in FIGS. 7, 9, 11 and 13 and are described as being generated in flow chart 200 where the data array graphically represented in FIGS. 6-7 corresponds with block 204, the data array graphically represented in FIG. 9 corresponds with block 206, the data array graphically represented in FIG. 11 corresponds with block 208, the data array graphically represented in FIG. 13 corresponds with block 210.

Two computations can be performed on the 2D numerical arrays of data generated from the original interferometric phase shifted images. For example, if four phase shifted images are generated with a phase shift of 90 degrees between each image, four phase shifted images can be acquired as illustrated in block 202 of FIG. 2. It should be realized, however, that any number of images can be generated and acquired. The two computations performed provide two new data sets: phase data (plotted and graphically represented in FIGS. 7 and 8) and a phase modulation data (plotted and graphically represented in FIGS. 9 and 10). Each illustrated plot represents corresponding 2D numerical array of data that corresponds with the intensity value of each pixel. With a set of four acquired images, this 2D numerical array of data for each plot is represented by $I_1$, $I_2$, $I_3$ and $I_4$. These data sets are then used to generate the 3D map of the surface using mathematical operations in accordance with interferometric methods.

Figure 7:
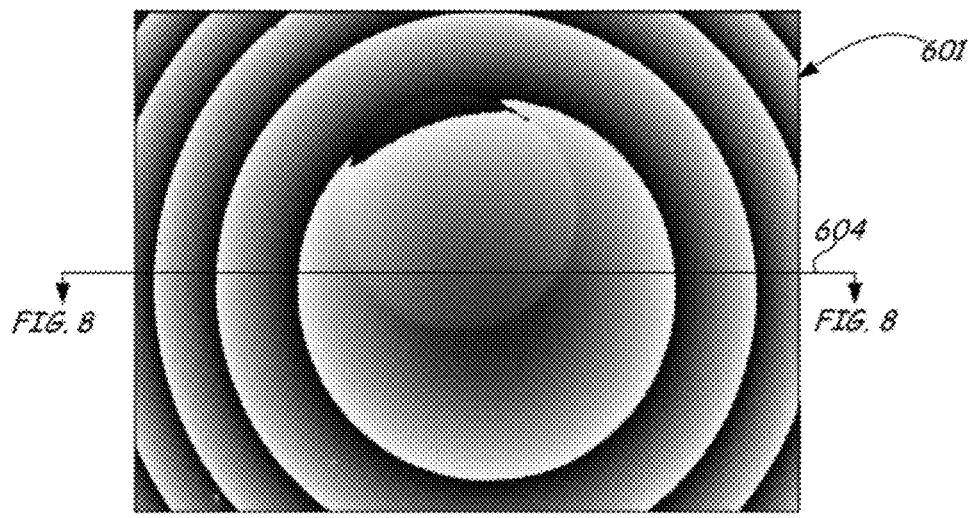
FIG. 7 illustrates an example phase plot representing phase data.
Figure 8:
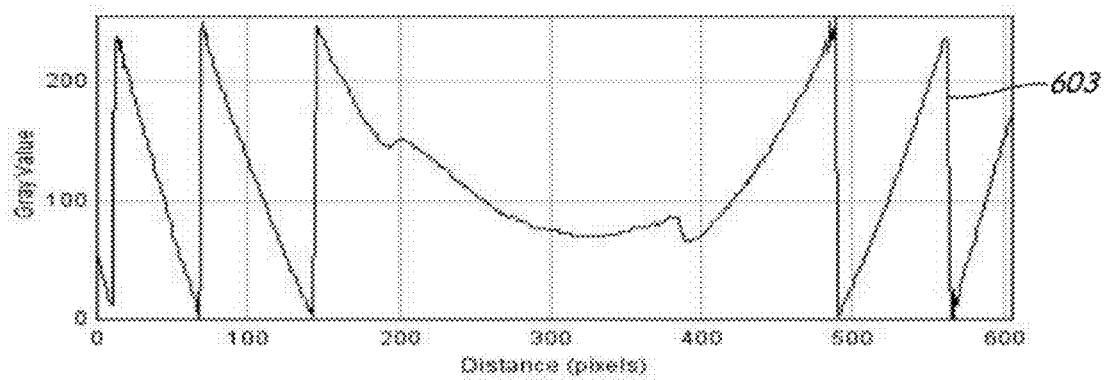
FIG. 8 is a graphical representation of intensity values of select pixels of phase data represented on the representative phase plot illustrated in FIG. 7.

Phase data graphically represented in FIG. 8 and pictorially represented in the phase plot of FIG. 7 are calculated as:

$$\text{Phase}(x, y) = \arctan\left(\frac{I_4 - I_2}{I_1 - I_3}\right)$$

where $I_1$, $I_2$, $I_3$ and $I_4$ represent the 2D numerical array of data for each of the example four acquired images.

Figure 9:
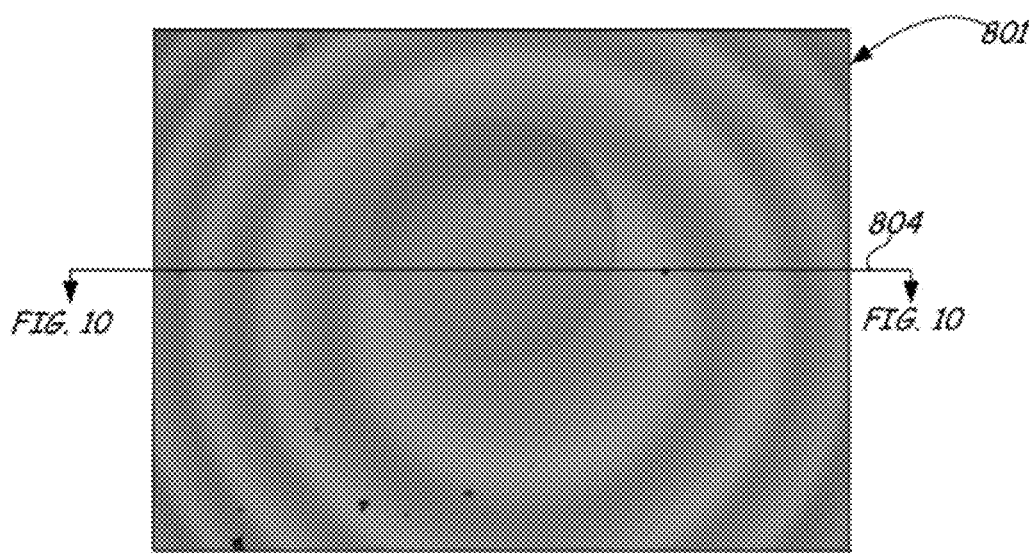
FIG. 9 illustrates an example phase modulation plot representing phase modulation data.

The phase modulation data represents the strength of the interferometric signal at each of the pixels. Very small defects or defects with very rough surfaces produce little or no interferometric signal (low modulation). Phase modulation data graphically represented in FIG. 10 and pictorially represented in the phase modulation plot of FIG. 9 are calculated as:

$$\text{PhaseModulation}(x, y) = \frac{2\sqrt{(I_1 - I_3)^2 + (I_2 - I_4)^2}}{I_1 + I_2 + I_3 + I_4}$$

where $I_1$, $I_2$, $I_3$ and $I_4$ represent the 2D numerical array of data for each of the four acquired images.

As previously discussed, FIG. 7 illustrates a phase plot 601 illustrating a two-dimensional numerical array of phase data. FIG. 8 illustrates intensity values for select pixels along line 604 in plot 601 of FIG. 7. Basically, data represented across line 604 in the FIG. 7 is converted into grey scale intensity values where each pixel in plot 601 corresponds exactly to a location or value 603 in the graphical representation of phase data illustrated in FIG. 8.

Figure 10:
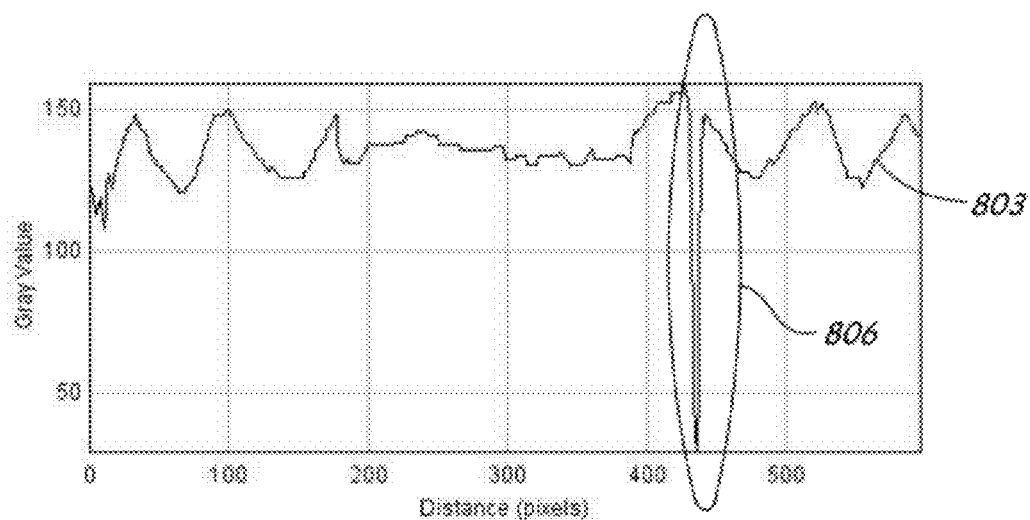
FIG. 10 is a graphical representation of intensity values of select pixels of phase modulation data on the representative phase modulation plot illustrated in FIG. 9.

As previously discussed, FIG. 9 illustrates a phase modulation plot 801 illustrating a two-dimensional numerical array of phase modulation data. FIG. 10 illustrates intensity values for select pixels along line 804 in plot 801 of FIG. 8. Basically, data represented across line 804 in FIG. 9 is converted into grey scale intensity values where the intensity value of each pixel corresponds exactly to the amount of phase modulation that took place at that pixel location or value 803 in the graphical representation of phase modulation data illustrated in FIG. 10. For example, light pixels correspond to a large amount of phase modulation taking place at that pixel location and dark pixels correspond to a smaller amount of modulation taking place at that pixel location. When a small defect is present on the surface being tested it may significantly absorb or scatter the phase information being reflected back from that location. As a result, the phase modulation will be very low for pixel locations that correspond to the location of a defect 806 on the sample. Low phase modulation will be indicated as a dark pixel value on plot 801 for that location.

Without the need for any other data, the phase modulation data or intermediate data set can be ran on a two-dimensional defect detection algorithm, illustrated in block 114, to identify locations of the dark pixels in the phase modulation plot 801. These pixel locations correspond to possible defect locations on the sample being measured.

Figure 11:
FIG. 11 illustrates an example image of an unwrapped phase plot representing unwrapped phase data.
Figure 12:
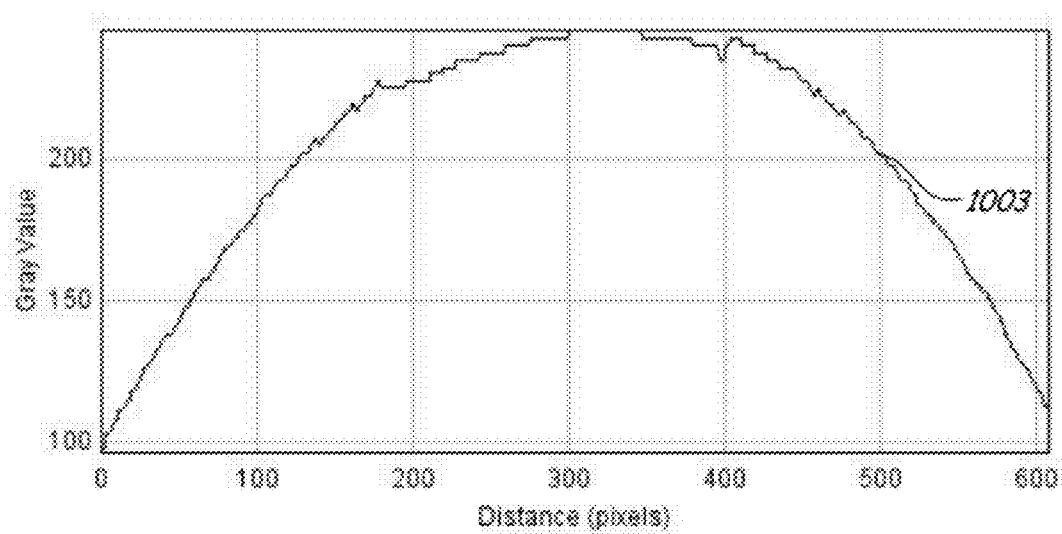
FIG. 12 is a graphical representation of intensity values of select pixels of unwrapped phase data on the representative unwrapped phase plot illustrated in FIG. 11.

Otherwise, the information from the 2D numerical array of phase data (FIG. 8) and the 2D numerical array of phase modulation data (FIG. 10) is combined to generate unwrapped phase data pictorially represented in the plot illustrated in FIG. 11 and graphically represented in FIG. 12. The unwrapped phase data is generated by removing the $2\pi$ discontinuities present in the phase and phase modulation data. Although other methods of phase unwrapping exist, in one embodiment, a method can be used to process each row of the phase and phase modulation data to find any jumps in phase of $2\pi$ and then add or subtract it to all following pixels to generate a continuous surface.

The unwrapped phase plot can be displayed as a grey scale intensity graph (FIG. 12) where the intensity value of each pixel corresponds exactly to the height (z-axis) position of the corresponding pixel location on the sample. For example values 1003 can include high values corresponding to light pixels on the sample being tested and low values 1003 corresponding to dark pixels on the sample being tested. The unwrapped phase data set will be used to generate the actual 3D map of the surface as it contains the height value for each pixel location in the image.

In fiber optic connector endface testing, the nominal shape of the sample is known to be a spherical surface. In one embodiment, the nominal shape of the sphere is subtracted from the unwrapped phase data to generate the subtracted data as pictorially represented in plot 1201 (FIG. 13) as illustrated in process block 1210 in FIG. 2. In another embodiment, the method is to break up the data sets into various regions, such as along line 1204 in FIG. 13, and perform the subtraction of each region separately. For example the core 310 and the cladding 312 (as illustrated in FIG. 3) can be processed as separate regions to allow for better fitting and then recombined for processing. The subtracted data can be displayed as grey scale intensity values 1203 where the intensity value of each pixel corresponds exactly to the height (z-axis) position of the corresponding pixel location on the sample. For example light pixels correspond to a high point on the sample and the dark pixels correspond to a low point on the sample being tested. This data set can be used to generate the subtracted 3D map of the surface with the nominal shape of the spherical surface removed.

Any points in the data set that deviate substantially from the nominal mean value of the data appear as either light or dark points. These light or dark points correspond to possible defects 1206 at that particular pixel location. Without any other data, the subtracted spherical data set can be processed by the two-dimensional defect detection algorithm as illustrated in block 214 (FIG. 2) as a 2D numerical array to identify locations of possible defects.

Besides the two-dimensional defect detection (block 214) using just the phase modulation data to detect defect locations in one embodiment and using just the subtracted spherical data to detect defect locations, in another embodiment, both intermediate data sets (the phase modulation data generated by process block 206 and the subtracted spherical data generated by process block 210) can both be used find defects. At block 214, the 2D defect detection algorithm perform defect detection on the phase modulation data and then on the subtracted spherical data. The 2D defect detection algorithm can use both data sets to identify and record pixels that have values that are either substantially higher or lower than the nominal average of the given data set on a plot. Such resulting defect locations are consolidated as illustrated in block 216 and plotted on plot 1401 illustrated in FIG. 15. There are numerous methods and combination of methods available that are able to efficiently perform this process, such as "blob" analysis as previously discussed. As illustrated in the 3D intensity plot of phase modulation data of FIG. 16, "blob" analysis is typically performed by thresholding the grey scale values so all pixels below a threshold are black as illustrated at lead line 1406 in FIG. 16 and all above the threshold are white (also illustrated in FIG. 16). The "blob" analysis routine then looks for connected white pixels and labels each set of connected pixels as blobs 1402 and 1403 illustrated in FIG. 15. These blobs correspond to the defects present.

Figure 15:
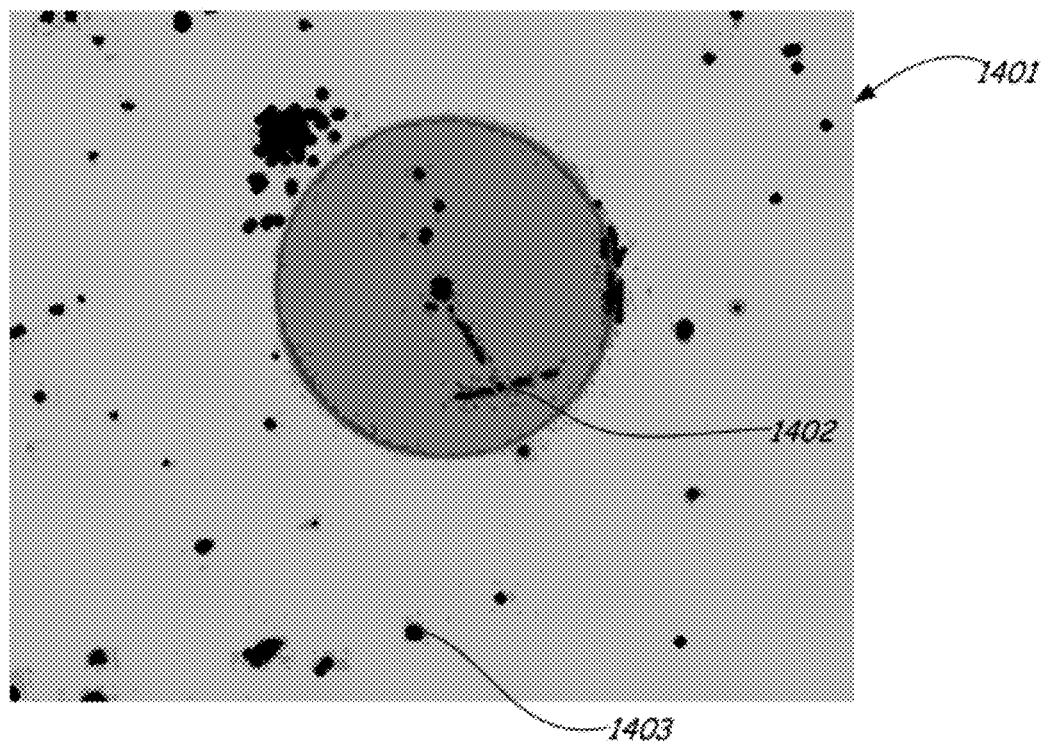
FIG. 15 illustrates an example image illustrating the resulting defect locations on the endface of the optical fiber specimen.
Figure 16:
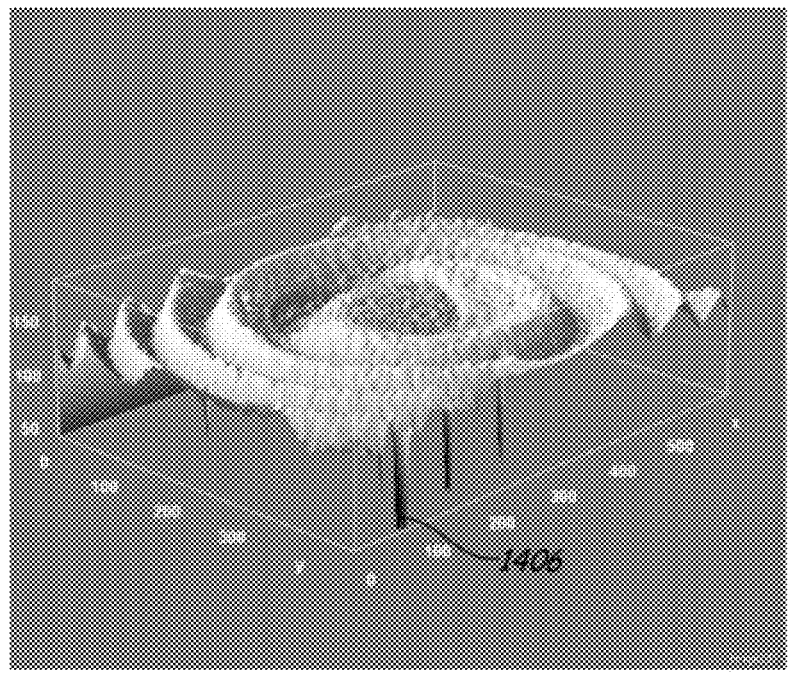
FIG. 16 illustrates an example three-dimensional intensity plot representing the phase modulation data.

The consolidation process illustrated in block 216 can form a list of defects that also include any previously identified defects detected in previous defect detection processes. The results of the defect detection processes are evaluated as illustrated in block 218. The values stored, for example on a storage memory, about each defect include the location of the defect, the shape of the defect and the height relative to the average surface and average intensity difference. At block 222, the resulting defects, such as defects 1402 and 1403 of FIG. 15, are displayed on a display 108 (FIG. 1) graphically as an image of the optical fiber specimen, such as the image illustrated in FIG. 15.

The spherical subtracted data generated in block 210 based on data generated in blocks 204, 206 and 208 is used in the normal process of generating a 3D topographical map as illustrated in block 212. Therefore, the 3D results can also be displayed on display 108 of FIG. 1.

It should be noted that to the extent that the present method is described in the context of optical fibers, the present invention is applicable to other types of microscopic optical surfaces, such as lens arrays and other suitable surfaces.

The invention claimed is:

1. A computing system comprising:
    an interferometer configured to generate at least two phase shifted fringe images of an optical fiber specimen;
    a processor configured to:
        acquire the at least two phase shifted fringe images from the interferometer;
        generate a first intermediate data set using the at least two acquired phase shifted fringe images, the first intermediate data set being a two-dimensional numerical array of pixel intensity values, each pixel intensity value of the first intermediate data set corresponding with a location on the optical fiber specimen; and
        identify non-geometric surface defects on the optical fiber specimen by selecting pixel intensity values from the first intermediate data set that substantially deviate from a nominal mean pixel intensity value, the nominal mean pixel intensity value being derived from pixel intensity values adjacent the select pixel intensity values of the first intermediate data set.

2. The computing system of claim 1, wherein the first intermediate data set comprises phase modulation data.

3. The computing system of claim 2, wherein the processor is further configured to generate phase data based on the at least two acquired phase shifted images.

4. The computing system of claim 3, wherein the processor is further configured to:
    combine the phase data and the phase modulation data to generate unwrapped phase data; and
    subtract nominal spherical shape data of the optical fiber specimen from the unwrapped phase data to generate a second intermediate data set, the second intermediate data set being a two-dimensional numerical array of pixel intensity values, each pixel intensity value of the second intermediate data set corresponding with a location on the optical fiber specimen.

5. The computing system of claim 4, wherein the processor further identifies select pixel intensity values from the second intermediate data set that substantially deviate from a nominal mean pixel intensity value of adjacent pixel intensity values of the second intermediate data set.

6. The computing system of claim 5, wherein the processor is further configured to consolidate the select pixel intensity values from the first intermediate data set and the select pixel intensity values from the second intermediate data set using image processing techniques.

7. The computing system of claim 1, wherein the first intermediate data set comprises subtracted spherical data generated by the processor performing the steps of:
    combining the phase data and the phase modulation data to generate unwrapped phase data; and
    subtracting the nominal spherical shape data of the optical fiber specimen from the unwrapped phase data.

8. The computing system of claim 1, wherein the processor is further configured to display the optical fiber specimen and the identified surface defects in their corresponding locations on the optical fiber specimen.

9. The computing system of claim 1, wherein the select pixel intensity values from the first intermediate data set that substantially deviate from the nominal mean pixel intensity value comprise pixel intensity values that are substantially greater than or substantially less than the nominal mean pixel intensity value of the adjacent pixel intensity values.

10. A method of detecting defects on an optical fiber specimen, the method comprising:
    using a processor to:
        acquire at least two phase shifted fringe images of an optical fiber specimen as generated by an interferometer;
        generate phase modulation data based on the at least two acquired phase shifted fringe images, the phase modulation data being a first intermediate data set and having a two-dimensional numerical array of pixel intensity values, each pixel intensity value corresponding with a location on the optical fiber specimen; and
        select pixel intensity values from the first intermediate data set that substantially deviate from a nominal mean pixel intensity value of adjacent pixel intensity values in the first intermediate data set to identify non-geometric surface defects on the optical fiber specimen.

11. The method of claim 10, further comprising identifying select pixel intensity values from a second intermediate data set that substantially deviate from a nominal mean pixel intensity value of adjacent pixel intensity values in the second intermediate data, the second intermediate data set generated by:
   combining the phase modulation data with phase data to generate unwrapped phase data, the phase data generated from the at least two acquired phase shifted fringe images; and
   subtracting the nominal spherical shape data of the optical fiber specimen from the unwrapped phase data.

12. The method of claim 11, further comprising consolidating the select pixel intensity values from the first intermediate data set and the select pixel intensity values from the second intermediate data set using image processing techniques.

13. The method of claim 12, further comprising quantifying the consolidated pixel intensity values into a set of defects that correspond with locations on the optical fiber specimen and displaying the optical fiber specimen and the defects on a display.

14. The method of claim 10, wherein the select pixel intensity values from the first intermediate data set that substantially deviate from the nominal mean pixel intensity value comprise pixel intensity values that are substantially less than the nominal mean pixel intensity value of the adjacent pixel intensity values.

15. The method of claim 14, wherein the select pixel intensity values that are substantially less than the nominal mean pixel intensity value of the adjacent pixel intensity values comprise dark pixels.

16. A method of detecting defects on an optical fiber specimen, the method comprising:
   using a processor to:
      acquire at least two phase shifted images of an optical fiber specimen as generated from an interferometer;
      generate phase data based on the at least two acquired phase shifted images;
      generate phase modulation data based on the at least two acquired phase shifted images;
      combine the phase data and the phase modulation data to generate unwrapped phase data;
      subtract the nominal spherical shape data of the optical fiber specimen from the unwrapped phase data to generate a first intermediate data set, the first intermediate data set being a two-dimensional numerical array of pixel intensity values, each pixel intensity value corresponding with a location on the optical fiber specimen; and
      select pixel intensity values from the first intermediate data set that substantially deviate from a nominal mean pixel intensity value of adjacent pixel intensity values to identify non-geometric surface defects on the fiber optical specimen.

17. The method of claim 16, wherein the phase modulation data comprises a second intermediate data set, the second intermediate data set being a two-dimensional numerical array of pixel intensity values, each pixel intensity value corresponding with a location on the optical fiber specimen.

18. The method of claim 17, further comprising identifying select pixel intensity values from the second intermediate data set that substantially deviate from a nominal mean pixel intensity value of adjacent pixel intensity values in the second intermediate data.

19. The method of claim 18, further comprising:
   consolidating the select pixel intensity values from the first intermediate data set and the select pixel intensity values from the second intermediate data set;
   quantifying the consolidated pixel intensity values into a set of defects that correspond with locations on the optical fiber specimen; and
   displaying the optical fiber specimen and the defects on a display.

20. The method of claim 16, wherein the select pixel intensity values of the first intermediate data set that substantially deviate from the nominal mean pixel intensity value of the adjacent pixel intensity values comprise pixel intensity values that are substantially greater than the nominal mean pixel intensity value of the adjacent pixel intensity values.

* * * * *

UNITED STATES PATENT AND TRADEMARK OFFICE
CERTIFICATE OF CORRECTION

| | |
|---|---|
| PATENT NO. | : 8,306,760 B1 |
| APPLICATION NO. | : 12/488993 |
| DATED | : November 6, 2012 |
| INVENTOR(S) | : Peter D. Koudelka et al. |

Page 1 of 1

It is certified that error appears in the above-identified patent and that said Letters Patent is hereby corrected as shown below:

Column 5

Line 9, delete "FIGS. 6-7" and insert --FIG. 7--.

Signed and Sealed this
Twelfth Day of March, 2013

Teresa Stanek Rea
*Acting Director of the United States Patent and Trademark Office*